United States Patent
Schmieding et al.

(10) Patent No.: US 7,837,708 B2
(45) Date of Patent: Nov. 23, 2010

(54) ACCELERATED HEALING WITH INTRAOPERATIVE COMBINATION OF SUTURE AND AUTOGENOUS BLOOD COMPONENTS

(75) Inventors: Reinhold Schmieding, Naples, FL (US); R. Donald Grafton, Naples, FL (US)

(73) Assignee: Arthrex, Inc., Naples, FL (US)

( * ) Notice: Subject to any disclaimer, the term of this patent is extended or adjusted under 35 U.S.C. 154(b) by 535 days.

(21) Appl. No.: 11/112,003

(22) Filed: Apr. 22, 2005

(65) Prior Publication Data

US 2005/0240225 A1    Oct. 27, 2005

Related U.S. Application Data

(60) Provisional application No. 60/564,241, filed on Apr. 22, 2004.

(51) Int. Cl.
- A61B 17/04    (2006.01)
- A61F 13/00    (2006.01)
- A61K 9/70    (2006.01)
- A61K 35/14    (2006.01)

(52) U.S. Cl. .................... 606/228; 424/443; 424/529

(58) Field of Classification Search ............. 606/228, 606/229, 230, 231; 424/443, 444, 529–534; 427/2.31; 128/898
See application file for complete search history.

(56) References Cited

U.S. PATENT DOCUMENTS

| | | | |
|---|---|---|---|
| 2,493,943 A * | 1/1950 | Bower | 606/229 |
| 2,615,450 A * | 10/1952 | Bower | 606/230 |
| 4,061,134 A * | 12/1977 | Samuels et al. | 600/36 |
| 4,714,457 A * | 12/1987 | Alterbaum | 494/37 |
| 5,165,938 A * | 11/1992 | Knighton | 424/532 |
| 5,226,877 A * | 7/1993 | Epstein | 604/35 |
| 5,585,007 A * | 12/1996 | Antanavich et al. | 210/782 |
| 5,610,148 A * | 3/1997 | Brown | 514/21 |
| 5,773,033 A * | 6/1998 | Cochrum et al. | 424/530 |
| 5,795,571 A * | 8/1998 | Cederholm-Williams et al. | 424/94.64 |
| 6,811,777 B2 * | 11/2004 | Mishra | 424/93.72 |
| 6,955,682 B2 * | 10/2005 | Luthra et al. | 606/213 |
| 2002/0179537 A1 * | 12/2002 | Sukavaneshvar et al. | 210/723 |
| 2003/0229376 A1 * | 12/2003 | Sandhu | 606/214 |
| 2005/0252867 A1 * | 11/2005 | Baugh et al. | 210/782 |
| 2006/0286289 A1 * | 12/2006 | Prajapati et al. | 427/2.31 |

* cited by examiner

*Primary Examiner*—(Jackie) Tan-Uyen T Ho
*Assistant Examiner*—Dianne Dornbusch
(74) *Attorney, Agent, or Firm*—Dickstein Shapiro LLP

(57) ABSTRACT

A suture combined intraoperatively with autogenous blood components. At least one strand of suture is placed into a sterile container. Blood obtained from a patient is separated, using a centrifuge, for example, to retrieve certain healing components such as autogenous growth factors, to obtain an autogenous blood suspension. The autogenous blood suspension is added to the sterile container containing the strand of suture. The suture wicks up biologic components of the autogenous blood suspension to produce an enhanced suture. Surgical repairs using the enhanced suture are conducted by suturing a tear to itself or to bone, for example. Post-operatively, the biologic components leach from the suture to accelerate healing of the repair.

9 Claims, 1 Drawing Sheet

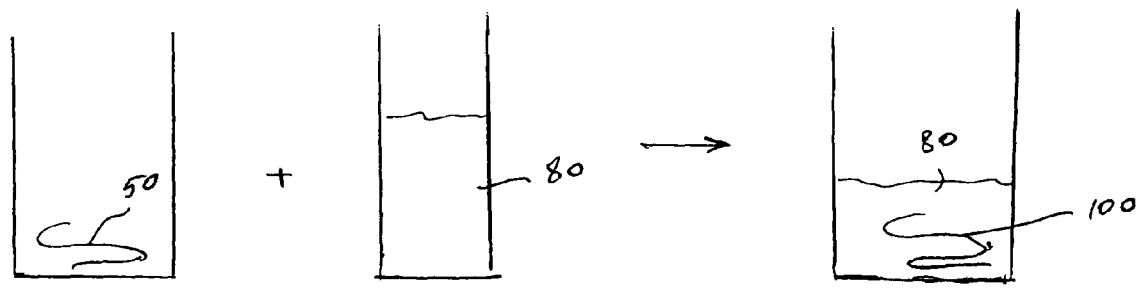
FIGURE

ACCELERATED HEALING WITH INTRAOPERATIVE COMBINATION OF SUTURE AND AUTOGENOUS BLOOD COMPONENTS

This application claims the benefit of U.S. Provisional Application No. 60/564,241, filed Apr. 22, 2004, the entire disclosure of which is incorporated by reference herein.

FIELD OF THE INVENTION

The present invention relates to surgical suturing and, more specifically, to methods and apparatus for performing surgical suturing using suture combined intraoperatively with autogenous blood components.

BACKGROUND OF THE INVENTION

Surgical suturing is used to repair torn tissue. It is known to provide packaged suture to surgeons with medically useful materials included in the suture, such as human epidermal growth factor. Limitations of the known methods include the storage stability of the materials included in the suture and patient immunological compatibility.

SUMMARY OF THE INVENTION

The present invention provides a suture that is combined intraoperatively with autogenous blood components. At least a strand of suture is placed into a sterile container. Blood obtained from a patient is separated, using a centrifuge, for example, to retrieve certain healing components such as autogenous growth factors, to obtain an autogenous blood suspension. The autogenous blood suspension is added to the sterile container containing the strand of suture. The suture wicks up biologic components of the autogenous blood suspension to produce an enhanced suture. The surgeon effects surgical repairs using the enhanced suture by suturing a tear to itself or torn tissue to bone, for example. Post-operatively, the biologic components leach from the suture to accelerate healing of the repair, for example.

The invention also provides a method of conducting suturing by employing a suture that is combined intraoperatively with autogenous blood components such as platelet-rich-plasma. The method comprises the steps of: (i) providing at least a strand of suture into a sterile container; (ii) obtaining an autogenous blood suspension comprising healing components such as growth factors from blood obtained from a patient; (iii) adding the autogenous blood suspension to the sterile container containing the suture to allow the suture to soak in the autogenous blood suspension and to produce an enhanced suture; and (iv) effecting a surgical repair employing the enhanced suture.

Other features and advantages of the present invention will become apparent from the following description of the invention, which refers to the accompanying drawing.

BRIEF DESCRIPTION OF THE DRAWING

The sole FIGURE illustrates a simplified process for obtaining a suture combined intraoperatively with autogenous blood components in accordance with an embodiment of the present invention.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a system for combining suture with medically useful materials without concern for the storage stability or patient compatibility. The combination can promote faster healing, for example, when used in surgical suturing of tissue. As explained below, suture is placed into a sterile container and blood obtained from a patient is separated to retrieve certain healing components such as platelet-rich-plasma, to obtain an autogenous blood suspension. The autogenous blood suspension is added to the sterile container containing the suture to allow the suture to soak in the autogenous blood suspension to produce an enhanced suture. The enhanced suture is subsequently employed in surgical repairs, promoting the healing of the repair and promoting tissue growth.

The term "growth factor" as used in the present application is intended to include all factors, such as proteinaceous factors, for example, which play a role in the induction or conduction of growth of tissue, ligaments, bone, cartilage or other tissues associated with bone or joints. In particular, these growth factors can include, for example, bFGF, aFGF, EGF (epidermal growth factor), PDGF (platelet-derived growth factor), IGF (insulin-like growth factor), TGF-$\beta$. I through III, including the TGF-$\beta$. superfamily (BMP-1 through 12, GDF 1 through 12, dpp, 60A, BIP, OF).

The term "endoscopy" encompasses arthroscopy, laparoscopy, hysteroscopy, among others, and endoscopic surgery involves the performance of surgical procedures within a patient's body through small openings as opposed to conventional open surgery through large incisions.

The term "suture" or "strand of suture" as used in this application is intended to encompass both non-absorbable as well as bio-absorbable sutures.

The drawing FIGURE illustrates an enhanced strand of suture 100 of the present invention. The enhanced strand of suture 100 is obtained by combining intraoperatively at least one strand of suture 50 with autogenous blood components 80. Initially, a strand of suture 50 is placed by a member of the surgical team into a sterile environment, for example a sterile container. Suture 50 may comprise a variety of materials including collagen, surgical gut, silk, cotton, polyolefins such as polypropylene, polyamides, polyesters such as polyethylene terephthalate, polyglycolic acid, glycolide-lactide copolymer, etc. Suture 50 may have a monofilament structure, suitable for knot-tying and knot-holding or, alternatively, a multifilament braided structure.

Blood obtained from the patient is separated, using a centrifuge, for example, to retrieve certain healing components such as growth factors, to obtain an autogenous blood suspension. The autogenous blood suspension comprises autogenous growth factors as defined above, such as platelet-rich plasma (referred to hereinafter as "PRP"), optionally in combination with hyaluronic acid (HY acid). In a preferred embodiment, the term "growth factor" includes autogenous growth factors produced from a patient's own blood, preferably PRP obtained by a centrifugation process. In an exemplary embodiment, PRP is prepared using PRP concentration kits such as the SmartPreP Kit sold by Harvest Technologies Corporation of Plymouth, Mass.

Optionally, the autogenous blood suspension may comprise additional lubricants and/or antiseptic chemicals and/or antibiotics. In this case, other solution excipients such as buffer salts, sugars, anti-oxidants and preservatives to maintain the bioactivity of the PRP and a proper pH of the autogenous blood suspension may be also employed. The additional lubricants and/or the antiseptics and/or the antibiotics will typically be present in the autogenous blood suspension in a predetermined concentration range, which will be dependent upon the particular tissue site and application, as well as the specific activity of the antiseptic and/or the antibiotic. The antibiotics may be selected from the group consisting of a neosporin, vancomycin and gentamycin, and combinations thereof.

The autogenous blood suspension may further comprise one or more additional components which promote or enhance the wound healing effectiveness of the autogenous growth factors. As such, site-specific hybrid proteins may be incorporated in the autogenous blood suspension to maximize the availability of the autogenous growth factors at the tissue to be sutured and/or to potentiate wound healing.

According to another embodiment of the present invention, the autogenous blood suspension may additionally comprise anticoagulants such as, for example, citrate, acid-citrate dextrose (ACD), citrate-phosphate-dextrose (CPD), or ethylene diamine tetra-acetic acid (EDTA). Heparin may be also added in an amount sufficient for the prevention of thrombin activity during the processing steps. Proteolytic enzyme inhibitors, such as aprotinin s-aminocaproic acid or tranexamic acid may be added to prevent proteolytic degradation of the autogenous growth factors.

According to yet another embodiment of the present invention, the autogenous blood suspension may further comprise one or more vitamins such as vitamin E, vitamin A and other retinoids. Vitamins are known to have wound healing and anti-oxidant properties. Alternatively, or additionally, non-vitamin anti-oxidants may be included in the autogenous blood suspension. Non-limiting representative examples of such anti-oxidants include β-carotene.

As shown in the drawing FIGURE, the autogenous blood suspension 80 is added to the sterile container containing the suture 50. The suture wicks up biologic components of the autogenous blood suspension such as the autogenous growth factors to produce enhanced suture 100. The orthopedic surgeon effects surgical repairs using the enhanced suture by suturing a rotator cuff tear to itself or bone, for example. Post-operatively, the biologic components leach from the suture to accelerate healing of the repair, for example.

A method of providing an enhanced suture combined intraoperatively with autogenous blood components to be employed in a suturing process according to the present invention comprises the steps of: (i) providing at least a strand of suture 50 into a sterile container; (ii) obtaining an autogenous blood suspension 80 comprising healing components such as growth factors from blood obtained from a patient; (iii) adding the autogenous blood suspension 80 to the sterile container containing the suture to allow the suture to soak in the autogenous blood suspension and to produce an enhanced soaked suture 100; and (iv) effecting a surgical repair such as a suturing a rotator cuff tear to itself or bone by employing the enhanced suture 100.

Although the above exemplary embodiment has been described with reference to the suture soaked intraoperatively with autogenous blood components such as platelet-rich-plasma provided at a particular tissue repair site, such as a rotator cuff tear, the invention is not limited to this exemplary embodiment. Accordingly, the present invention has applicability to a suture soaked intraoperatively with autogenous growth factors employed during the suturing of various tissues and within repair sites corresponding to bone, soft tissue or osteochondral tissue, among others. The suture soaked intraoperatively with autogenous growth factors may be used for suturing during various endoscopic procedures, as well as during conventional open surgeries.

In addition, although the embodiments of the present invention have been described above with reference to a suture placed into a container and autogenous blood components which are subsequently added intraoperatively to the suture, the invention is not limited to these embodiments and also contemplates the addition of suture to a container having the autogenous blood components. Accordingly, although the present invention has been described in relation to particular embodiments, many other variations and modifications and other uses will become apparent to those skilled in the art.

The above description and the drawing FIGURE illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed is:

1. A method of suturing comprising:
   placing a length of suture into a sterile container;
   obtaining an autogenous blood component from a patient by centrifuging the patient's blood;
   adding an anticoagulant to the autogenous blood component to prevent coagulation of the autogenous blood component and keep the blood component in suspension; and
   intraoperatively adding the uncoagulated autogenous blood component to the length of suture into the sterile container to obtain a suture soaked with the autogenous blood component.

2. The method of claim 1, further comprising suturing tissue of the patient using the length of suture soaked with the autogenous blood component.

3. The method of claim 1, wherein the autogenous blood component comprises a growth factor.

4. The method of claim 3, wherein the growth factor is platelet-rich plasma.

5. A surgical suture comprising:
   a length of suture prepared for surgical use in a patient in accordance with the method of claim 1, including the step of obtaining an autogenous blood component from the patient by centrifuging the patient's blood and adding an anticoagulant to the autogenous blood component to form an anticoagulant added to autogeneous blood material obtained from the patient to form an uncoagulated autogenous blood material, the suture being impregnated with the uncoagulated autogenous blood material intraoperatively and prior to surgical use.

6. A surgical method comprising:
   providing at least one strand of suture into a container;
   obtaining an autogenous blood suspension from a patient by centrifuging the patient's blood;
   adding an anticoagulant to the autogenous blood suspension to prevent coagulation of the autogenous blood suspension and keep blood in suspension;
   subsequently, adding the uncoagulated autogenous blood suspension to the at least one strand of suture in the container to obtain a soaked suture; and
   suturing tissue of the patient using the soaked suture combined with the autogenous blood suspension.

7. The method of claim 6, wherein the autogenous blood suspension includes a component selected from the group consisting of autogenous growth factors, hyaluronic acid, antiseptics, antibiotics, and vitamins.

8. The method of claim 6, wherein the autogenous blood suspension comprises platelet-rich plasma.

9. The method of claim 6, wherein the at least one strand of suture comprises a material selected from the group consisting of collagen, surgical gut, silk, cotton, polyolefins, polyamides, polyesters, polyglycolic acid and glycolide-lactide copolymer.

* * * * *